US007091486B1

(12) United States Patent
McCord et al.

(10) Patent No.: US 7,091,486 B1
(45) Date of Patent: Aug. 15, 2006

(54) METHOD AND APPARATUS FOR BEAM CURRENT FLUCTUATION CORRECTION

(75) Inventors: Mark A. McCord, Los Gatos, CA (US); Alan D. Brodie, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/938,841

(22) Filed: Sep. 9, 2004

(51) Int. Cl.
*G01N 23/00* (2006.01)
*G21K 7/00* (2006.01)

(52) U.S. Cl. .................. 250/311; 250/306; 250/307
(58) Field of Classification Search .................. None
See application file for complete search history.

(56) References Cited

U.S. PATENT DOCUMENTS

| | | | | |
|---|---|---|---|---|
| 4,211,924 A | * | 7/1980 | Muller et al. | 250/311 |
| 4,937,458 A | * | 6/1990 | Fujikura | 250/492.2 |
| 5,254,857 A | * | 10/1993 | Ross et al. | 250/310 |
| 5,449,915 A | * | 9/1995 | Yamada et al. | 250/397 |
| 6,169,282 B1 | * | 1/2001 | Maeda et al. | 250/310 |
| 6,426,501 B1 | * | 7/2002 | Nakagawa | 250/310 |
| 6,555,830 B1 | | 4/2003 | Mankos et al. | |
| 6,617,597 B1 | | 9/2003 | Hilton | |

FOREIGN PATENT DOCUMENTS

WO   WO 03/032361 A1   4/2003

\* cited by examiner

*Primary Examiner*—Nikita Wells
*Assistant Examiner*—Anthony Quash
(74) *Attorney, Agent, or Firm*—Okamoto & Benedicto LLP

(57) ABSTRACT

One embodiment disclosed relates to an electron beam imaging apparatus. An electron source is configured to generate an electron beam, and a beam-limiting aperture is configured to block a portion of the electron beam and to allow transmission of another portion of the electron beam through the aperture. A first detector is configured to detect scattered electrons emitted by the aperture due to the blocked portion of the electron beam. The imaging apparatus may also include a second detector configured to detect scattered electrons emitted by the sample due to impingement of the transmitted portion of the electron beam. A gain control device may also be included to adjust a gain of a detected signal derived from the second detector using a control signal derived from the first detector. Another embodiment disclosed relates to an electron beam lithography apparatus. The lithography apparatus may adjust a pixel dwell time based on a control signal derived from the scattered electrons emitted by the aperture.

22 Claims, 4 Drawing Sheets

METHOD AND APPARATUS FOR BEAM CURRENT FLUCTUATION CORRECTION

BACKGROUND OF THE INVENTION

1. Field of the Invention

The present invention relates to the correction of beam current fluctuations in electron beam inspection tools and other similar apparatus.

2. Description of the Background Art

In electron beam inspection systems, defects are often detected by comparing the signals from corresponding image pixels in a chip (die) being tested and a reference standard. The reference standard may be an electronic database (for die-to-database inspection) or a reference die (for die-to-die inspection). A defect is typically detected when the signals between the die and reference differ by more than a threshold amount.

Beam current fluctuations may cause errors in such defect detection. These beam current fluctuations may be caused, for example, by emission noise from cold field or Schottky electron emission sources, or from other causes.

A conventional technique for correcting beam current fluctuations uses a circuit connected to the beam-limiting aperture to measure an electrical current from the aperture. This electrical current is due to the electrons being absorbed by the aperture. From the current measured, a beam current may be inferred. Changes in the current measured are used to infer changes in the beam current.

SUMMARY

One embodiment of the invention relates to an electron beam imaging apparatus. An electron source is configured to generate an electron beam, and a beam-limiting aperture is configured to block a portion of the electron beam and to allow transmission of another portion of the electron beam through the aperture. A first detector is configured to detect scattered electrons emitted by the aperture due to the blocked portion of the electron beam. The imaging apparatus may also include a second detector configured to detect scattered electrons emitted by the sample due to impingement of the transmitted portion of the electron beam. A gain control device may also be included to adjust a gain of a detected signal derived from the second detector using a control signal derived from the first detector.

Another embodiment of the invention relates to an electron beam lithography apparatus. The lithography apparatus may adjust a pixel dwell time based on a control signal derived from the scattered electrons emitted by the aperture.

DETAILED DESCRIPTION

As discussed above, a conventional technique measures an electrical current due to electrons being absorbed by an aperture to infer a beam current. Unfortunately, this conventional technique is suitable to detect fluctuations only within a limited bandwidth of frequencies. In particular, detecting high-frequency (for example, above a few kilohertz) fluctuations is problematic. Hence, the conventional technique does not allow for correction of higher-frequency variations in the beam current. This bandwidth limitation appears to be due to the low current levels and high stray capacitance in the conventional technique.

The present invention relates to an improved technique to correct for beam fluctuations in charge-particle metrology equipment, lithography equipment, or inspection equipment, or other similar tools. Instead of measuring an electrical current due to electrons being absorbed by the aperture, an embodiment of the present invention uses a detector mounted above the aperture to collect and measure secondary and/or backscattered electrons. The secondary and/or backscattered electrons are emitted due to the impingement of part of the primary beam (the part being blocked) onto the aperture. In a preferred embodiment, the detector is mounted just above the beam-limiting aperture, and the detector comprises a high-speed electron detector. High-speed electron detectors include, for example, Everhart-Thornley detectors, PIN diode based detectors, and microchannel plate detectors.

The detector collects the secondary and/or the backscattered signal from that part of the beam being blocked by the aperture. The collected signal is converted into a voltage signal that is proportional to the (nearly) instantaneous current being blocked by the aperture. Assuming that the fluctuations in the beam current are not spatially correlated at the aperture plane, this signal is a reasonably accurate proxy for the actual beam current.

Figure 1:
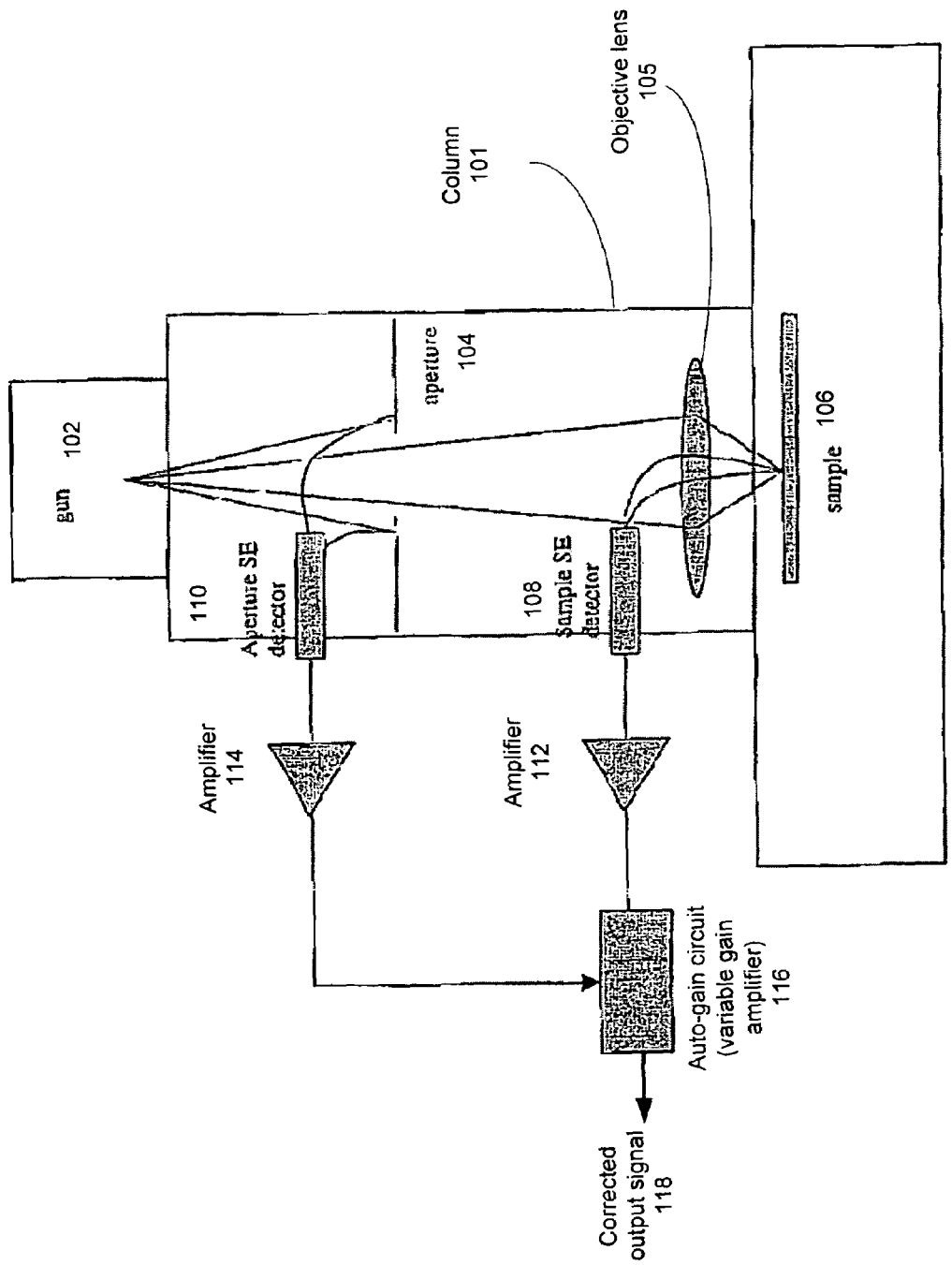
FIG. 1 is a cross-sectional diagram of an apparatus for beam current fluctuation correction in accordance with an embodiment of the invention.
Figure 2:
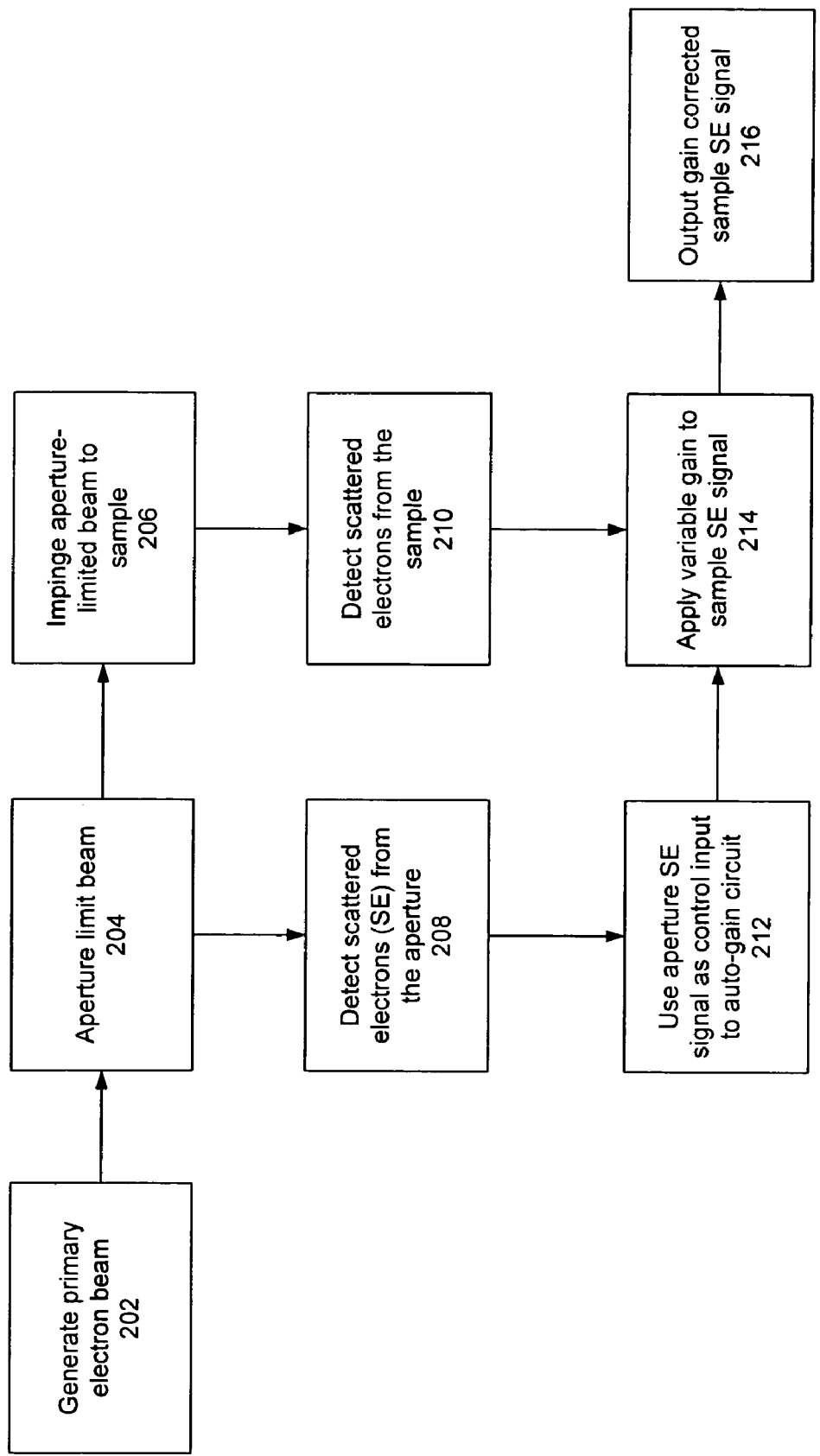
FIG. 2 is a flow chart depicting a method of beam current fluctuation correction in accordance with an embodiment of the invention.

An embodiment of the invention is described in relation to the cross-sectional diagram of FIG. 1 and the flow chart of FIG. 2. The diagram of FIG. 1 shows an apparatus for beam current fluctuation correction, while the flow chart of FIG. 2 depicts a method of beam current fluctuation correction.

In accordance with an embodiment of the invention, the apparatus comprises an electron beam column 101. An electron gun 102 near the top portion of the column 101 generates 202 a primary electron beam. The primary electron beam is aperture limited 204 by a beam-limiting aperture 104. In other words, a portion of the primary beam is blocked by the electron-opaque portion of the aperture 104, and a portion of the primary beam goes through the opening of the aperture 104. The portion going through the opening of the aperture 104 is focused by an objective lens 105 onto the sample or specimen 106.

The apparatus includes at least two detectors. The first detector is a sample scattered electron (SE) detector 108. The sample SE detector 108 may comprise a detector configured to detect 210 secondary electrons and/or backscattered electrons that are emitted due to impingement 206 of the primary beam onto the sample 106. The second detector is an aperture SE detector 110. The aperture SE detector 110 may comprise a detector configured to detect 208 secondary and/or backscattered electrons that are emitted due to blocking of the primary beam by the opaque portion of the aperture. While the sample SE detector 108 may be found in a conventional apparatus, the aperture SE detector 110 is advantageously included in accordance with an embodiment of the invention.

The aperture SE detector 110 preferably comprises a high-speed electron detector, such as an Everhart-Thornley detector, a PIN diode based detector, or a microchannel plate detector. An alternative implementation would use an annular-shaped detector in the region between the beam-limiting aperture and the electron source. Such an annular detector would be oriented to directly detect part of the beam current coming from the gun that would otherwise be intercepted by the beam-limiting aperture.

Another embodiment of the invention may use an annular-shaped detector in the aperture plane. The annular-shaped detector would be configured so that the incident beam is transmitted through the opening of the detector. Such a detector in the aperture plane would detect primary electrons from the electron gun that impinge upon the annular-shaped detector.

In accordance with an embodiment of the invention, the apparatus further includes an auto-gain circuit 116. The detected signal from the sample SE detector 108 is fed through an amplifier circuit 112 to a first input of the auto-gain circuit 116. The detected signal from the aperture SE detector 110 is fed through an amplifier circuit 114 to a second input of the auto-gain circuit 116. The auto-gain circuit 116 may include a variable gain amplifier configured to amplify the sample SE signal. The aperture SE signal may be used 212 as a control input to the auto-gain circuit 116 so as to control the variable gain applied 214 to the sample SE signal. The auto-gain circuit 116 outputs 216 the gain corrected sample SE signal 118. This corrected output 118 may then be used to generate an image of the sample area for metrology or inspection purposes. The image so generated being corrected for nearly instantaneous brightness variations in the primary beam.

Figure 3:
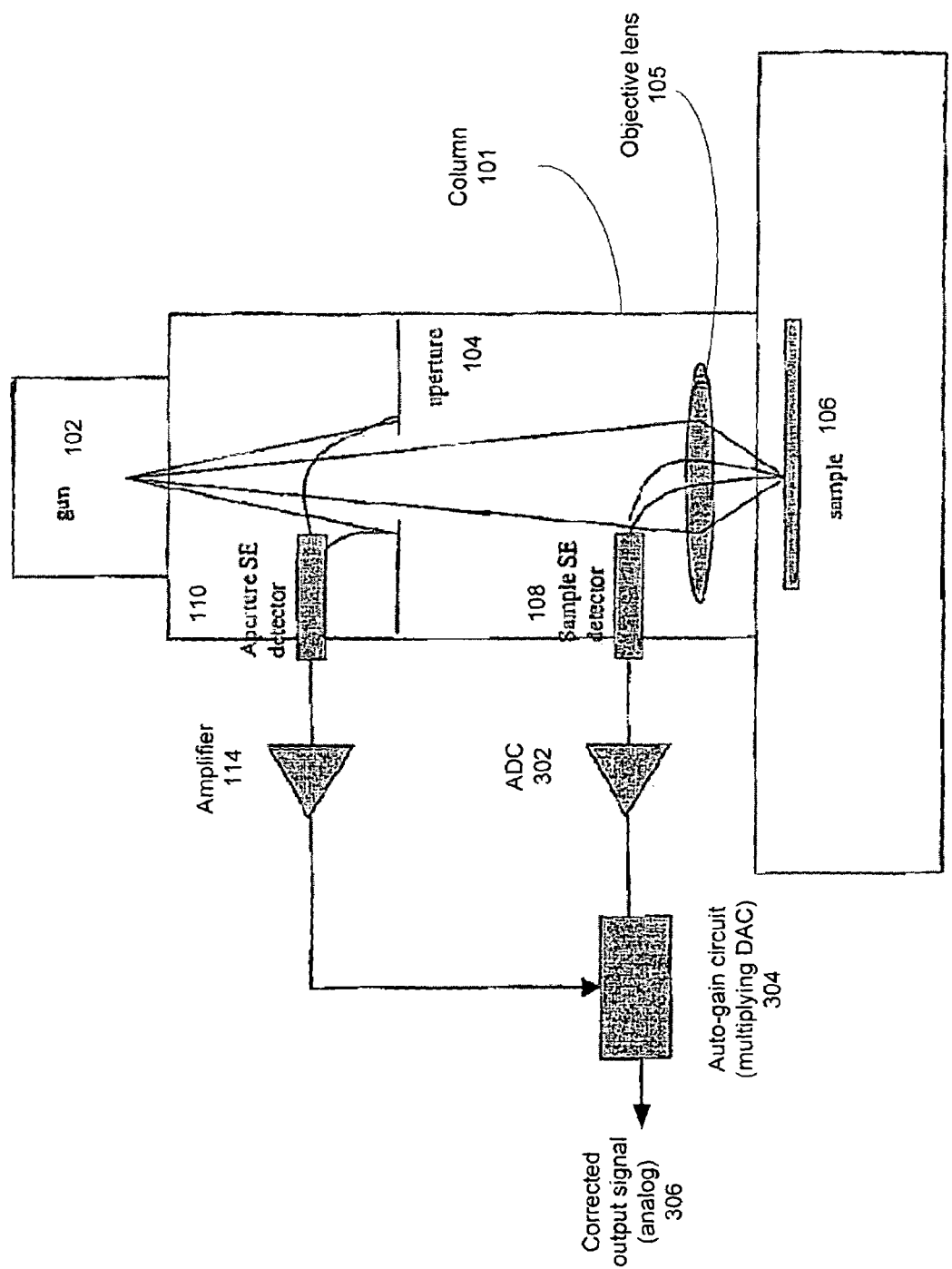
FIG. 3 is a cross-sectional diagram of an apparatus for beam current fluctuation correction in accordance with another embodiment of the invention.

The above-described embodiment utilizes a variable gain amplifier circuit. Another embodiment of the invention is described in relation to the cross-sectional diagram of FIG. 3. The apparatus of FIG. 3 is similar to the apparatus of FIG. 1, with a few differences. The apparatus of FIG. 3 includes an analog-to-digital converter (ADC) circuit 302 to convert the sample SE signal from analog to digital form. In digital form, the magnitude of the sample SE signal is represented using digital bits. Furthermore, the auto-gain circuit 304 is configured with a multiplying DAC. The multiplying DAC is configured to receive as input the digitized sample SE signal and to multiply that signal by an amount proportional to the aperture SE signal. The output is the gain corrected sample SE signal 306 (in analog form). This corrected output 306 may then be used to generate image data of the sample area for metrology or inspection purposes. The image data so generated being corrected for nearly instantaneous brightness variations in the primary beam.

An alternative embodiment may not use such an auto-gain circuit. Instead, the gain correction may be done in the digital domain during processing of the image data. In this digital domain embodiment, digital image data would be processed so as to effectively adjust the gain of the sample SE image data based on the amplitude of the aperture SE signal at the corresponding time.

Another embodiment of the invention utilizes an aperture SE detector in a lithography system. While traditional lithographic processes utilize electromagnetic energy in the form of ultraviolet light (or x-rays) for selective exposure of the resist, charged particle beams have also been used for high resolution lithographic resist exposure. In particular, electron beams have been used since the low mass of electrons allows relatively accurate control of an electron beam at relatively low power and relatively high speed. Electron beam lithographic systems may be categorized as electron-beam direct write (EBDW) lithography systems and electron beam projection lithography systems.

In EBDW lithography, the substrate is sequentially exposed by means of a focused electron beam. The focused beam writes the desired structure on the substrate (by controlled blanking or in a vector scan method). In electron beam projection lithography, analogously to optical lithography, a mask or portion thereof is illuminated and is imaged on a reduced scale on a wafer by means of projection optics.

In accordance with an embodiment of the invention, an EBDW or an electron beam projection lithography apparatus may be configured with an aperture SE detector above a beam-limiting aperture in the apparatus. In an electron beam projection lithography apparatus, the aperture SE detector may alternatively be positioned above the mask.

Figure 4:
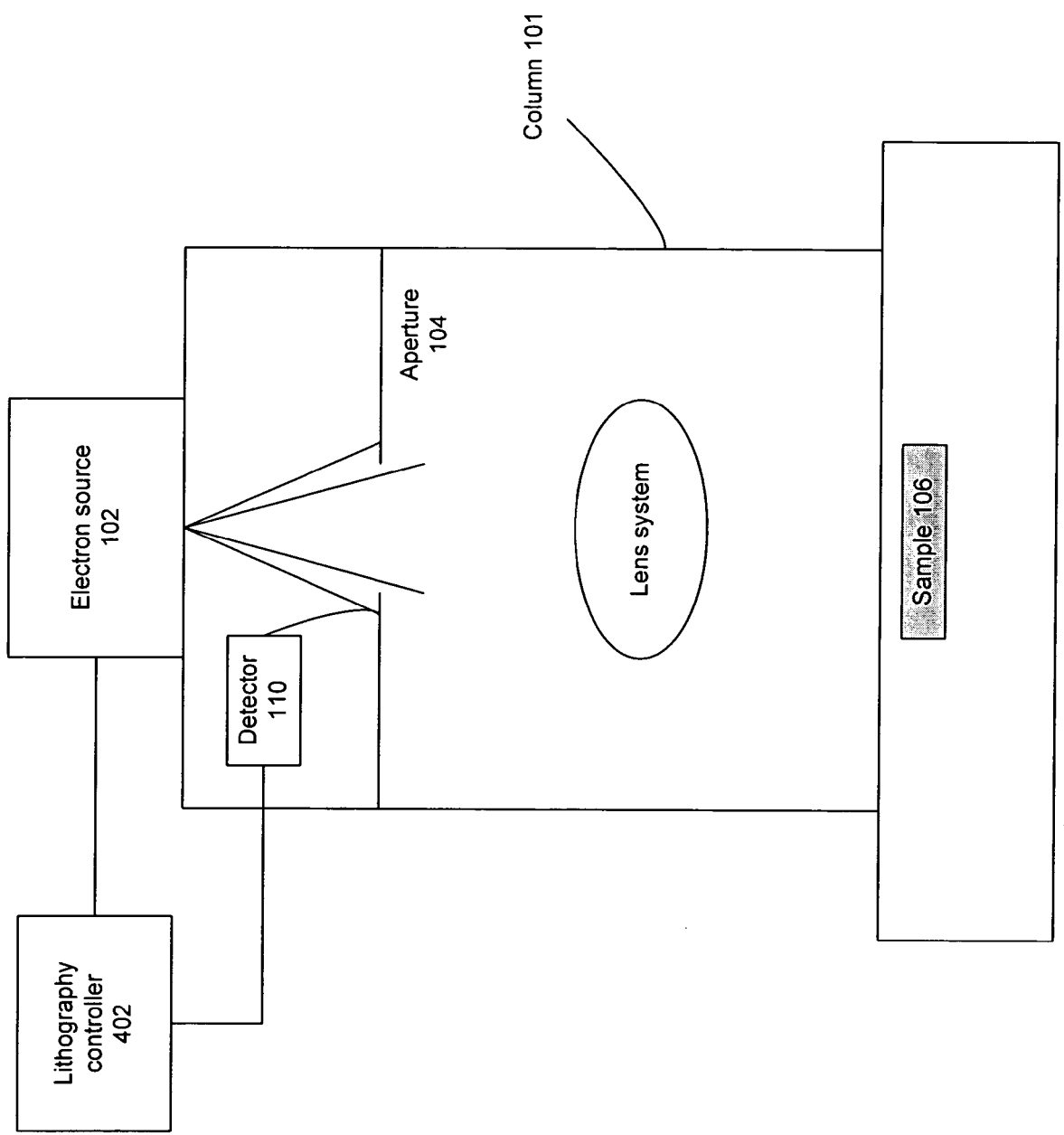
FIG. 4 is a cross-sectional diagram of an electron beam lithography apparatus including beam current fluctuation correction in accordance with an embodiment of the invention.

FIG. 4 is a cross-sectional diagram of an electron beam lithography apparatus including beam current fluctuation correction in accordance with an embodiment of the invention. The signal from the detector 110 may be fed back to the lithography controller 402 and used to adjust a pixel dwell time of the beam. A brighter beam would cause the pixel dwell time to be adjusted to a proportionally shorter time. A dimmer beam would cause the pixel dwell time to be adjusted to a proportionally longer time.

As discussed above, an embodiment of the invention advantageously allows for correction of image brightness or dose variation due to beam current fluctuations. The correction may be done at a high-speed (at a rate approaching or exceeding the pixel speed of the system) due to the use of a high-speed aperture SE detector (instead of measuring current from the aperture). As a result, lower-noise images may be obtained in a shorter period of time for imaging systems, or more precise linewidth control may be obtained in lithographic systems.

Another embodiment of the invention utilizes the output of the aperture detector as basis for feedback to adjust the beam current of an electron beam apparatus. In other words, the beam current may be adjusted by feedback to a electron gun controller of a signal based on the detected scattered electrons emitted by the aperture. This embodiment may be used in metrology, inspection, and lithography applications. Prior gun control systems have used feedback from an electrical current measured from the aperture, but not feedback from electrons scattered from the aperture.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An electron beam apparatus for imaging a substrate surface, the apparatus comprising:
    an electron source configured to generate an electron beam;
    a beam-limiting aperture configured to block a portion of the electron beam while at a same time allowing transmission of another portion of the electron beam through the aperture to subsequently impinge upon the substrate surface for said imaging;
    a first scattered electron (SE) detector for gain adjustment which is configured to detect a first signal from scattered electrons emitted from a surface of the aperture due to impingement onto the surface by the blocked portion of the electron beam;
    a second scattered electron (SE) detector for generating image data which is configured to detect a second signal from scattered electrons emitted from the substrate surface due to impingement onto the substrate surface by the transmitted portion of the electron beam; and
    a gain control device configured to use the first signal to adjust a gain level for the second signal, where the first signal is detected at a same time as the second signal.

2. The apparatus of claim 1, wherein the first scattered electron detector comprises a high-speed detector.

3. The apparatus of claim 2, wherein the detector comprises an Everhart-Thornley detector.

4. The apparatus of claim 2, wherein the detector comprises a PIN diode based detector.

5. The apparatus of claim 2, wherein the detector comprises a microchannel plate detector.

6. The apparatus of claim 2, wherein the detector comprises an annular shape through which the electron beam is transmitted.

7. The apparatus of claim 1, further comprising:
    an objective lens for focusing the transmitted portion of the electron beam onto the substrate surface.

8. The apparatus of claim 7, wherein the sample comprises a semiconductor substrate.

9. The apparatus of claim 1, wherein the gain control device adjusts the gain in an analog signal domain.

10. The apparatus of claim 9, wherein the gain control device adjusts the gain using a variable gain amplifier.

11. The apparatus of claim 9, wherein the gain control device adjusts the gain using a multiplying digital-to-analog converter.

12. The apparatus of claim 1, wherein the gain control device adjusts the gain in a digital signal domain.

13. The apparatus of claim 1, wherein the apparatus comprises an automated electron beam inspection apparatus.

14. The apparatus of claim 1, wherein the apparatus comprises a critical-dimension scanning electron microscope (CD-SEM).

15. A method of monitoring a beam current and correcting an image for fluctuations in the beam current, the method comprising:
    generating an electron beam using an electron source;
    blocking a portion of the electron beam with an opaque part of an aperture;
    allowing transmission of another portion of the electron beam through a hole of the aperture;
    detecting a first signal of scattered electrons emitted from the opaque part of the aperture due to impingement onto the the opaque part by the blocked portion of the electron beam;
    detecting a second signal of scattered electrons emitted from a target substrate being imaged by the transmitted portion of the electron beam; and
    using the first signal to adjust a gain of the second signal, where the first signal is detected at a same time as the second signal.

16. The method of claim 15, wherein the method is performed in an imaging apparatus, and wherein the method further comprises:
    focusing the transmitted portion of the electron beam onto the target substrate.

17. The method of claim 16, wherein the imaging apparatus comprises an electron beam metrology tool configured to measure features on a substrate.

18. The method of claim 16, wherein the imaging apparatus comprises an electron beam inspection tool configured to inspect manufactured substrates.

19. The method of claim 15, wherein the method further comprises:
    adjusting a beam current by feedback to a electron gun controller of the first signal.

20. An electron beam apparatus for imaging a substrate comprising:
    means for generating an electron beam using an electron source;
    an aperture configured to block a portion of the electron beam while at a same time allowing transmission of another portion of the electron beam through the aperture to impinge upon the substrate;
    a first means for detecting a first signal of scattered electrons emitted from a surface of the aperture due to impingement onto the surface of the aperture by the blocked portion of the electron beam;
    a second means for detecting a second signal of scattered electrons emitted from the substrate being imaged by the transmitted portion of the electron beam; and
    a gain control device configured to use the first signal to adjust a gain level for the second signal, where the first signal and the second signal are detected at a same time.

21. The apparatus of claim 20, wherein the scattered electrons comprise secondary electrons.

22. The apparatus of claim 20, wherein the scattered electrons comprise backscattered electrons.

* * * * *